United States Patent [19]

Blösl et al.

[11] Patent Number: 4,613,457
[45] Date of Patent: Sep. 23, 1986

[54] 2-METHYL PENTANOIC ACID ESTERS AND PERFUME COMPOSITIONS CONTAINING THEM

[75] Inventors: Siegfried Blösl, Duesseldorf; Klaüs Bruns, Krefeld-Traar; Ulf-Armin Schaper, Krefeld, all of Fed. Rep. of Germany

[73] Assignee: Henkel Kommanditgesellschaft auf Aktien, Duesseldorf, Fed. Rep. of Germany

[21] Appl. No.: 578,340

[22] Filed: Feb. 9, 1984

[30] Foreign Application Priority Data

Feb. 25, 1983 [DE] Fed. Rep. of Germany ....... 3306560

[51] Int. Cl.$^4$ .......................... A61K 7/46; C07C 69/02
[52] U.S. Cl. ................................ 252/522 R; 252/8.6; 252/174.11; 560/231; 560/254; 560/259; 560/261
[58] Field of Search ............... 252/8.6, 174.11, 522 R; 424/49, 69; 560/254, 261, 231, 259, 284

[56] References Cited

U.S. PATENT DOCUMENTS

| | | | |
|---|---|---|---|
| 3,455,988 | 7/1969 | Duke et al. | 560/1 |
| 3,966,986 | 6/1976 | Hunter et al. | 426/534 |
| 4,126,585 | 11/1978 | Conrad et al. | 560/261 X |
| 4,267,075 | 5/1981 | Schaper et al. | 252/522 R |
| 4,387,047 | 6/1983 | Sundt et al. | 560/261 X |

FOREIGN PATENT DOCUMENTS

| | | | |
|---|---|---|---|
| 0034334 | 8/1981 | European Pat. Off. | 560/261 |
| 2530227 | 7/1975 | Fed. Rep. of Germany . | |
| 2513808 | 10/1975 | Fed. Rep. of Germany | 560/261 |
| 0000588 | 8/1979 | PCT Int'l Appl. | 252/522 R |
| 1306017 | 2/1973 | United Kingdom . | |

OTHER PUBLICATIONS

Arctander, *Perfume and Flavor Chemicals*, vol. II, Monograph 2161 (1967).
Chemical Abstracts, Ninth Collective Index, American Chemical Society, Columbus Ohio, US; * 78: 120206d*.
Synthetic Attractants Screened in the Field as Lures for Chloropidae, Ann. Entomol. Soc. America, 1973, vol. 66(2), pp. 262-265.
European Search Report.

*Primary Examiner*—Anton H. Sutto
*Attorney, Agent, or Firm*—Ernest G. Szoke; Henry E. Millson, Jr.

[57] ABSTRACT

Methyl pentanoic acid esters corresponding to the formula

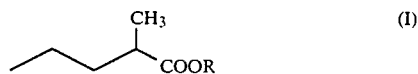

wherein R is an olefinically unsaturated, straight-chain or branched-chain or carbocyclic hydrocarbon group, a phenyl or alkyl substituted phenyl group, a phenyl substituted alkyl group, or a phenyl substituted alkenyl group, wherein R contains from 3 to 9 carbon atoms, are valuable perfumes having strong, generally vegetably odor notes and outstanding persistence. They are produced by esterifying 2-methyl pentanoic acid with an unsaturated or carbocyclic alcohol or phenol containing radicals R corresponding to the general formula.

The compounds can be effectively combined with other perfumes and standard perfume ingredients to form new compositions. The methyl pentanoic acid ester content thereof generally amounts to between about 1 and about 50% by weight.

6 Claims, No Drawings

2-METHYL PENTANOIC ACID ESTERS AND PERFUME COMPOSITIONS CONTAINING THEM

BACKGROUND OF THE INVENTION

German Application No. 25 30 227 discloses lower alkyl esters of 2-methyl pentenoic acid, optionally in admixture with lower alkyl esters of 2-methyl pentanoic acid, which can be used as an aromatic essence for liquid and solid foods and the like or as a perfume for cosmetic and hygienic preparations.

DESCRIPTION OF THE INVENTION

It has now been found that 2-methyl pentanoic acid esters corresponding to the following formula I

in which R is an olefinically unsaturated, straight-chain or branched-chain or carbocyclic hydrocarbon group; a phenyl or alkyl substituted phenyl group; or a phenyl substituted alkyl or phenyl substituted alkenyl group, in which R contains from 3 to 9, preferably from 5 to 9, carbon atoms, are valuable perfumes characterized by strong, generally vegetably odor notes and outstanding persistence.

The compounds are produced by esterifying 2-methyl pentanoic acid with an alcohol or phenol of the formula ROH, wherein R has the meaning given above. The esterification reaction can be carried out by known esterification methods.

In the above formula, examples of the R group include propenyl, butenyl, hexenyl, nonenyl, 3-methyl-2-butenyl, 3-methyl-3-butenyl, cyclohexenyl, 3,5,5-trimethyl-2-cyclohexenyl (=isophoryl), 2,4(5)-dimethyl-4-cyclohexenyl methyl, benzyl, 3-phenyl-2-propenyl, phenyl, o-cresyl, and the 4-ethylphenyl radical. Radicals containing from 5 to 9 carbon atoms are particularly preferred.

One preferred method of producing, for example, 2-methyl pentanoic acid-3-methyl-2-butenyl ester comprises reacting 2-methyl pentanoic acid chloride with 3-methyl-2-buten-1-ol in the presence of pyridine. Other esters of formula I above can also be produced in this manner.

The 2-methyl pentanoic acid esters of formula I are distinguished by interesting and very different, mainly vegetably odor notes. These preferably include flowery and fruity notes and also odors of green or dried plants or parts thereof. A pungent secondary odor is noticeable with decreasing chain length, particularly below $C_5$. The compounds of the invention show outstanding persistence and can be combined very effectively with standard perfume ingredients and other perfumes to form novel compositions to which they also impart high persistence. The 2-methyl pentanoic acid esters of formula I are generally added to perfume compositions in a proportion of from about 1 to about 50% by weight. The compounds of formula I can be used for perfuming cosmetic preparations, such as creams, lotions, toilet water, aerosols, toilet soaps, mouthwash preparations etc. and also in extract perfumery. They can also be used for improving the odor of commercial products, such as detergents and cleaners or fabric softeners. For perfuming and odor improving use, the compounds of formula I can be used in quantities of from about 0.05 to about 2% by weight, based on the product as a whole.

The invention will be illustrated by the following examples, which are given for that purpose only, and not for purposes of limitation.

EXAMPLES

A. General Procedure 0.1 mole of 2-methyl pentanoic acid, 0.12 mole of unsaturated alcohol or phenol, 100 ml of cyclohexane and 0.1 g of p-toluene sulfonic acid are heated to the boiling point. The water released is azeotropically removed from the system. On completion of the reaction, the reaction mixture, cooled to room temperature, is washed first with 10% sodium hydroxide solution and then with a saturated sodium sulfate solution until it shows a neutral reaction, dried over sodium sulfate, concentrated in vacuo and distilled through a 20 cm packed column. Yields: 70–90% of the theoretical.

The following esters were produced by this general procedure:

1. 2-methyl pentanoic acid-3-phenyl-2-propenyl ester

| | |
|---|---|
| B.p.$_{0.09}$:99° C. | $n_D^{20} = 1.5163$ |
| $^1$H—NMR (CDCl$_3$) | δ = 7.26 ppm (5H,m) |
| | δ = 6.45 ppm (2H,m) |
| | δ = 4.73 ppm (2H,d) |
| odor: bitter almond note, green | |

2. 2-methyl pentanoic acid isophoryl ester

| | |
|---|---|
| B.p.$_{0.09}$:87° C. | $n_D^{20} = 2.4572$ |
| $^1$H—NMR (CDCl$_3$) | δ = 5.38 ppm (2H,m) |
| | δ = 2.43 ppm (1H,m) |
| Odor: saffron, tabacco, carob-bean note | |

3. 2-methyl pentanoic acid-3-hexenyl ester

| | |
|---|---|
| B.p.$_{21}$:111° C. | $n_C^{20} = 1.4348$ |
| $^1$H—NMR (CDCl$_3$) | δ = 5.5 ppm (2H,m) |
| | δ = 4.1 ppm (2H,t) |
| Odor: green, carbide, onion note | |

4. 2-methyl pentanoic acid-3-methyl-2-butenyl ester 0.1 mole of 2-methyl pentanoic acid chloride is added over a period of 1 hour while stirring and cooling with ice to 0.15 mole of 2-methyl-2-buten-1-ol and 0.1 mole of pyridine. After stirring for 1 hour, the mixture is poured into ice water acidified with HCl. The organic phase is then washed with aqueous Na$_2$CO$_3$-solution, dried and subjected to fractional distillation. Yield: 71% of the theoretical of 2-methyl pentanoic acid-3-methyl-2-butenyl ester

| | |
|---|---|
| B.p.$_{0.07}$:38° C. | $n_D^{20} = 1.4370$ |
| $^1$H—NMR (CDCl$_3$) | δ = 5.33 ppm (1H,m) |
| | δ = 4.58 ppm (2H,d) |
| Odor: elder blossom, juniper, blackcurrant. | |

B. Perfume Compositions (Fruity Wood Base)

| | |
|---|---|
| 2-methyl pentanoic acid-3-methyl-2-butenyl ester | 200 parts by weight |
| Boisambrene forte ® (Henkel) | 200 parts by weight |
| p-tert.-butyl cyclohexyl acetate | 150 parts by weight |

| -continued | |
|---|---|
| caryophyllin acetate | 100 parts by weight |
| 6-methyl ionone | 70 parts by weight |
| Linalool | 60 parts by weight |
| Cistus Oil (10% in diethyl phthalate) | 50 parts by weight |
| Galaxolid | 40 parts by weight |
| Patchouli oil | 30 parts by weight |
| Guaiyl acetate | 40 parts by weight |
| $C_{12}$—aldehyde (10% in diethyl phthalate) | 20 parts by weight |
| $C_{14}$—aldehyde (10% in diethyl phthalate) | 20 parts by weight |
| $C_{16}$—aldehyde (19% in diethyl phthalate) | 20 parts by weight |
| | 1,000 parts by weight |

What is claimed is:

1. A method of perfuming a product in need thereof comprising adding to the product from about 0.05 to about 2% by weight of 2-methyl pentanoic acid-2-phenyl-2-propenyl ester.

2. A method of perfuming a product in need thereof comprising adding to the product from about 0.05 to about 2% by weight of 2-methyl pentanoic acid isophoryl ester.

3. A perfume composition containing from about 1 to about 50% by weight, based on the weight of the composition, of 2-methyl pentanoic acid-3-phenyl-2-propenyl ester.

4. A perfume composition containing from about 1 to about 50% by weight, based on the weight of the composition, of 2-methyl pentanoic acid isophoryl ester.

5. 2-methyl pentanoic acid-3-phenyl-2-propenyl ester.

6. 2-methyl pentanoic acid isophoryl ester.

* * * * *